(12) United States Patent
McIntosh

(10) Patent No.: US 11,717,202 B2
(45) Date of Patent: Aug. 8, 2023

(54) MOBILE LAB-ON-A-CHIP DIAGNOSTIC SYSTEM

(71) Applicant: Foothold Labs Inc., Olathe, KS (US)

(72) Inventor: Sean McIntosh, Lawrence, KS (US)

(73) Assignee: Foothold Labs Inc., Olathe, KS (US)

( * ) Notice: Subject to any disclaimer, the term of this patent is extended or adjusted under 35 U.S.C. 154(b) by 459 days.

(21) Appl. No.: 16/846,095

(22) Filed: Apr. 10, 2020

(65) Prior Publication Data

US 2020/0323474 A1    Oct. 15, 2020

Related U.S. Application Data

(60) Provisional application No. 62/831,978, filed on Apr. 10, 2019.

(51) Int. Cl.
*G08B 23/00* (2006.01)
*A61B 5/15* (2006.01)
(Continued)

(52) U.S. Cl.
CPC .... *A61B 5/150358* (2013.01); *A61B 5/14532* (2013.01); *A61B 5/6898* (2013.01); *G01N 33/5438* (2013.01)

(58) Field of Classification Search
CPC .......... A61B 5/150358; A61B 5/14532; A61B 5/6898; A61B 5/1468; A61B 5/4845;
(Continued)

(56) References Cited

U.S. PATENT DOCUMENTS

| 4,715,237 A | 12/1987 | Kaempf et al. |
|---|---|---|
| 5,062,547 A | 11/1991 | Zahner et al. |

(Continued)

FOREIGN PATENT DOCUMENTS

| CN | 106732835 A | 5/2017 |
|---|---|---|
| EP | 2381250 A1 | 10/2011 |
| JP | 2013253962 A | 12/2013 |

OTHER PUBLICATIONS

International Search Report and Written Opinion dated Jul. 22, 2021 in International Patent Application No. PCT/US2021/026708, including Notification of Transmittal, 20 pages.

*Primary Examiner* — Anh V La
(74) *Attorney, Agent, or Firm* — Cooley LLP

(57) ABSTRACT

A testing system for conducting electrochemistry analysis of a specimen sample is provided. The testing system includes a testing receptacle device and a diagnostic device. The testing receptacle device includes a receptacle having an interior space defined therein and a lid configured to be secured on an upper end of the receptacle. The lid includes an opening extending into the receptacle and a cartridge slot for receiving a test sensor cartridge having a functionalized electrode strip with an electrode well contact point provided thereon. The diagnostic device is configured as a potentiostat or similar device and includes a docking port for receiving a lower end of the testing receptacle device. The testing system is configured for receiving a specimen sample through the opening in the receptacle lid and placing the specimen sample in contact with the electrode well contact point of the functionalized electrode strip.

16 Claims, 9 Drawing Sheets

(51) Int. Cl.
*A61B 5/00* (2006.01)
*A61B 5/145* (2006.01)
*G01N 33/543* (2006.01)

(58) Field of Classification Search
CPC .......... A61B 5/14507; A61B 5/150022; G01N 33/5438; G01N 27/28; G01N 27/26; G01N 33/483; B01L 2300/047; B01L 2300/0663; B01L 2300/0858; B01L 3/5029; B01L 3/508
USPC ............... 607/145; 340/573.1, 514, 603, 620
See application file for complete search history.

(56) References Cited

U.S. PATENT DOCUMENTS

| | | |
|---|---|---|
| 5,110,429 A | 5/1992 | Novotny et al. |
| 5,296,193 A | 3/1994 | Reger et al. |
| 5,512,131 A | 4/1996 | Kumar et al. |
| 5,686,829 A | 11/1997 | Girault |
| 5,861,097 A | 1/1999 | Schafer et al. |
| 6,153,101 A | 11/2000 | Schafer et al. |
| 6,182,517 B1 | 2/2001 | Zahner |
| 7,019,040 B2 | 3/2006 | Seubert et al. |
| 7,288,394 B2 | 10/2007 | Ostuni et al. |
| 7,753,238 B2 | 7/2010 | Kirschenbuhler et al. |
| 7,767,146 B2 | 8/2010 | Kirschenbuhler |
| 8,809,065 B2 | 8/2014 | Mutharasan et al. |
| 8,973,447 B2 | 3/2015 | Volckens et al. |
| 9,618,439 B2 | 4/2017 | Volckens et al. |
| 9,618,474 B2 | 4/2017 | Van et al. |
| 9,618,476 B2 | 4/2017 | Goldsmith |
| 9,765,395 B2 | 9/2017 | Goldsmith |
| 9,857,328 B2 | 1/2018 | Hoffman |
| 9,859,394 B2 | 1/2018 | Hoffman et al. |
| 10,006,910 B2 | 6/2018 | Hoffman |
| 10,020,300 B2 | 7/2018 | Hoffman |
| 10,139,270 B2 | 11/2018 | Mutharasan et al. |
| 10,395,928 B2 | 8/2019 | Pan et al. |
| 10,413,621 B2 | 9/2019 | Basilion et al. |
| 10,429,342 B2 | 10/2019 | Hoffman et al. |
| 10,429,381 B2 | 10/2019 | Hoffman |
| 10,494,670 B2 | 12/2019 | Van et al. |
| 10,607,989 B2 | 3/2020 | Hoffman |
| 10,737,855 B2 | 8/2020 | Christensen et al. |
| 10,751,986 B2 | 8/2020 | Lerner et al. |
| 10,759,157 B2 | 9/2020 | Lerner et al. |
| 10,811,539 B2 | 10/2020 | Van et al. |
| 10,875,339 B1 | 12/2020 | Claussen et al. |
| 10,876,210 B1 | 12/2020 | Claussen et al. |
| 10,903,319 B2 | 1/2021 | Pan et al. |
| 10,968,481 B2 | 4/2021 | Van et al. |
| 2002/0027085 A1 | 3/2002 | Stori et al. |
| 2003/0190259 A1* | 10/2003 | Alley ................ A61B 10/0051 422/411 |
| 2004/0082749 A1 | 4/2004 | Seubert et al. |
| 2004/0171135 A1 | 9/2004 | Ostuni et al. |
| 2004/0253150 A1 | 12/2004 | Kirschenbuhler |
| 2006/0003382 A1 | 1/2006 | Eckermann et al. |
| 2006/0045805 A1 | 3/2006 | Kirschenbuhler |
| 2007/0194055 A1 | 8/2007 | Kirschenbuhler et al. |
| 2008/0145908 A1 | 6/2008 | Ostuni et al. |
| 2009/0065357 A1 | 3/2009 | Glezer et al. |
| 2009/0081785 A1 | 3/2009 | Ho et al. |
| 2009/0090022 A1 | 4/2009 | Ho et al. |
| 2009/0118382 A1 | 5/2009 | Raskop et al. |
| 2010/0297687 A1 | 11/2010 | Mutharasan et al. |
| 2011/0027861 A1 | 2/2011 | Ho et al. |
| 2011/0097795 A1 | 4/2011 | Ho et al. |
| 2011/0171754 A1* | 7/2011 | Redmond ......... B01L 3/502715 422/68.1 |
| 2012/0207684 A1 | 8/2012 | Basilion et al. |
| 2012/0238008 A1 | 9/2012 | Henry et al. |
| 2012/0244606 A1* | 9/2012 | Takeshita ............ A61B 5/1486 435/287.1 |
| 2012/0269730 A1 | 10/2012 | Mirkin et al. |
| 2012/0302456 A1 | 11/2012 | Whitesides et al. |
| 2013/0059380 A1 | 3/2013 | Ho et al. |
| 2013/0133441 A1 | 5/2013 | Volckens et al. |
| 2013/0205902 A1 | 8/2013 | Mutharasan et al. |
| 2014/0120520 A1 | 5/2014 | Ho et al. |
| 2014/0360890 A1 | 12/2014 | Mutharasan et al. |
| 2015/0064723 A1 | 3/2015 | Mutharasan et al. |
| 2015/0143929 A1 | 5/2015 | Volckens et al. |
| 2015/0157009 A1 | 6/2015 | Ho et al. |
| 2015/0253296 A1 | 9/2015 | Christensen et al. |
| 2015/0307936 A1 | 10/2015 | Goldsmith |
| 2015/0309018 A1 | 10/2015 | Goldsmith |
| 2016/0025675 A1 | 1/2016 | Goldsmith |
| 2016/0052683 A1 | 2/2016 | Christensen et al. |
| 2016/0054312 A1 | 2/2016 | Goldsmith |
| 2016/0178569 A1 | 6/2016 | Hoffman et al. |
| 2016/0265047 A1 | 9/2016 | Van Rooyen et al. |
| 2017/0018626 A1 | 1/2017 | Hoffman et al. |
| 2017/0053908 A1 | 2/2017 | Hoffman |
| 2017/0059514 A1 | 3/2017 | Hoffman |
| 2017/0102358 A1 | 4/2017 | Hoffman |
| 2017/0218442 A1 | 8/2017 | Van Rooyen et al. |
| 2017/0307562 A1 | 10/2017 | Goldsmith |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0037952 A1 | 2/2018 | Goldsmith |
| 2018/0311664 A1 | 11/2018 | Lansing et al. |
| 2018/0315750 A1 | 11/2018 | Hoffman |
| 2018/0339292 A1* | 11/2018 | Katz ................ G01N 33/54366 |
| 2019/0120830 A1 | 4/2019 | Hoffman |
| 2019/0125316 A1* | 5/2019 | Tariyal ............... A61B 10/0045 |
| 2019/0181273 A1 | 6/2019 | Van Rooyen et al. |
| 2019/0262827 A1 | 8/2019 | Lalonde et al. |
| 2019/0351665 A1 | 11/2019 | Lerner et al. |
| 2020/0009271 A1 | 1/2020 | Basilion et al. |
| 2020/0025753 A1 | 1/2020 | Claussen et al. |
| 2020/0038866 A1 | 2/2020 | Henry et al. |
| 2020/0141931 A1 | 5/2020 | Hoffman |
| 2020/0181695 A1 | 6/2020 | Van Rooyen et al. |
| 2020/0215488 A1 | 7/2020 | Laubli et al. |
| 2020/0339322 A1 | 10/2020 | Christensen et al. |

\* cited by examiner

MOBILE LAB-ON-A-CHIP DIAGNOSTIC SYSTEM

CROSS-REFERENCE TO RELATED APPLICATIONS

This Application claims priority to U.S. Provisional Patent Application Ser. No. 62/831,978, filed on Apr. 10, 2019, to Sean McIntosh, entitled "Test Stand For Mobile Lab-On-A-Chip System,", the entire disclosure of which is incorporated herein by reference.

BACKGROUND OF THE INVENTION

Electrochemical technology is currently utilized to test specimen samples in order to determine the composition of the sample by identifying the sample's wave pattern or voltammogram using an electrochemical technique such as voltammetry, square wave voltammetry, chronoamperometry, or electrochemical impedance spectroscopy. These procedures can be used to provide lab-quality trace detection of explosives, narcotics, toxic industrial chemicals and other chemicals, each of which have a unique electrochemical signature. Advancements in electroanalytical instrumentation and electrochemistry technology have increased the accuracy and feasibility of sample testing through electrochemistry. However, currently employed electrochemistry testing systems require laboratory conditions and are expensive. As a result, such systems are not typically suitable to field applications where testing is often desirable, for example by law enforcement, military, customs, airport security and others.

Accordingly, a need exists for improved systems and devices that can allow for practical and cost-efficient electrochemistry testing of specimens samples in field applications.

BRIEF SUMMARY OF THE INVENTION

The present invention is directed generally to an electrochemistry testing system and testing device that can be used in connection with the testing and analysis of specimen samples of unidentified materials. The electrochemistry testing system and testing device can be used to identify unknown chemical compounds within a specimen sample by detecting electrochemical signatures unique to the chemical compounds therein to determine the specific identity of the specimen sample.

The electrochemistry testing system of the present invention can include a testing receptacle device and a diagnostic device. The testing system can further include a test sensor cartridge that is inserted into and used within the testing receptacle device. The test sensor cartridge can include a functionalized electrode strip having an electrode well contact point container thereon as commonly used in electrochemistry analysis.

The testing receptacle device can include a receptacle and a lid for enclosing an upper end of the receptacle. The receptacle can include a perimeter sidewall and a bottom wall defining an interior space therein. The lid can include an upper lid section and a lower lid section configured to fit together and be secured onto the upper end of the receptacle.

The receptacle can further include a swab guide configured to direct a specimen sample inserted into the testing receptacle device toward the electrode well contact point of the functionalized electrode strip contained within the interior space of the receptacle. The swab guide can include an angled surface wall extending inward from the perimeter sidewall at a downward angle toward the electrode well contact point of the functionalized electrode strip of the test sensor cartridge. The swab guide can further include a pair of fins or projections extending along the sides of the angled surface wall to define the horizontal sides of the swab guide.

The testing receptacle device lid can include openings defined through each of the upper lid section and the lower lid section to provide a continuous opening through the lid and into the interior space of the receptacle. The continuous opening can be aligned with the swab guide of the receptacle to allow a specimen sample to be inserted through the continuous opening and into the swab guide toward the electrode well contact point of the functionalized electrode strip of the test sensor cartridge. The lower lid section can include a cartridge slot for receiving a cartridge head portion of the test sensor cartridge and retain the test sensor cartridge within the testing receptacle device.

The diagnostic device can be configured as a diagnostic testing device, such as a potentiostat or galvanostat as commonly used in electrochemistry. The diagnostic device can incorporate software programming and circuitry configured to carry out the testing and scanning functionality of the testing system and can include programming that can store a library of electrochemical signatures for different types of chemicals, compounds and materials to enable the testing system to identify the composition of specimen samples tested. The diagnostic device can be configured to carry out one or more electrical techniques used with a potentiostat or galvanostat diagnostic device, including without limitation, cyclic voltammetry, square wave voltammetry, electrochemical impedance spectroscopy, and chronoamperometry.

The diagnostic device can further be configured as a test stand for receiving and holding the testing receptacle device. The diagnostic device can include a docking port that receives a lower end of the testing receptacle device and retains the testing receptacle device on the diagnostic device. The docking port can further include a connection port that places the testing receptacle device in electronic communication with the diagnostic device to facilitate the transfer of data between the testing receptacle device and the diagnostic device for conducting electrochemical analysis.

The testing system can be configured for use with a testing swab that can include a swab end portion and a swab handle. The swab end portion can have a specimen sample placed thereon and inserted into the testing receptacle device through the continuous opening defined through the lid. The swab end portion can be traversed through the swab guide and into contact with the electrode well contact point of the functionalized electrode strip. A current can then be ran through the functionalized electrode strip by means of the test sensor cartridge and the diagnostic device can carry out the electrochemistry analysis to determine the specific identity of the specimen sample.

Other aspects and advantages of the present invention will be apparent from the following detailed description of the preferred embodiments of the accompanying drawing figures.

DESCRIPTION OF THE SEVERAL VIEWS OF THE DRAWING

In the accompanying drawing, which forms a part of the specification and is to be read in conjunction therewith in which like reference numerals are used to indicate like or similar parts in the various views.

DETAILED DESCRIPTION OF THE INVENTION

Figure 1:
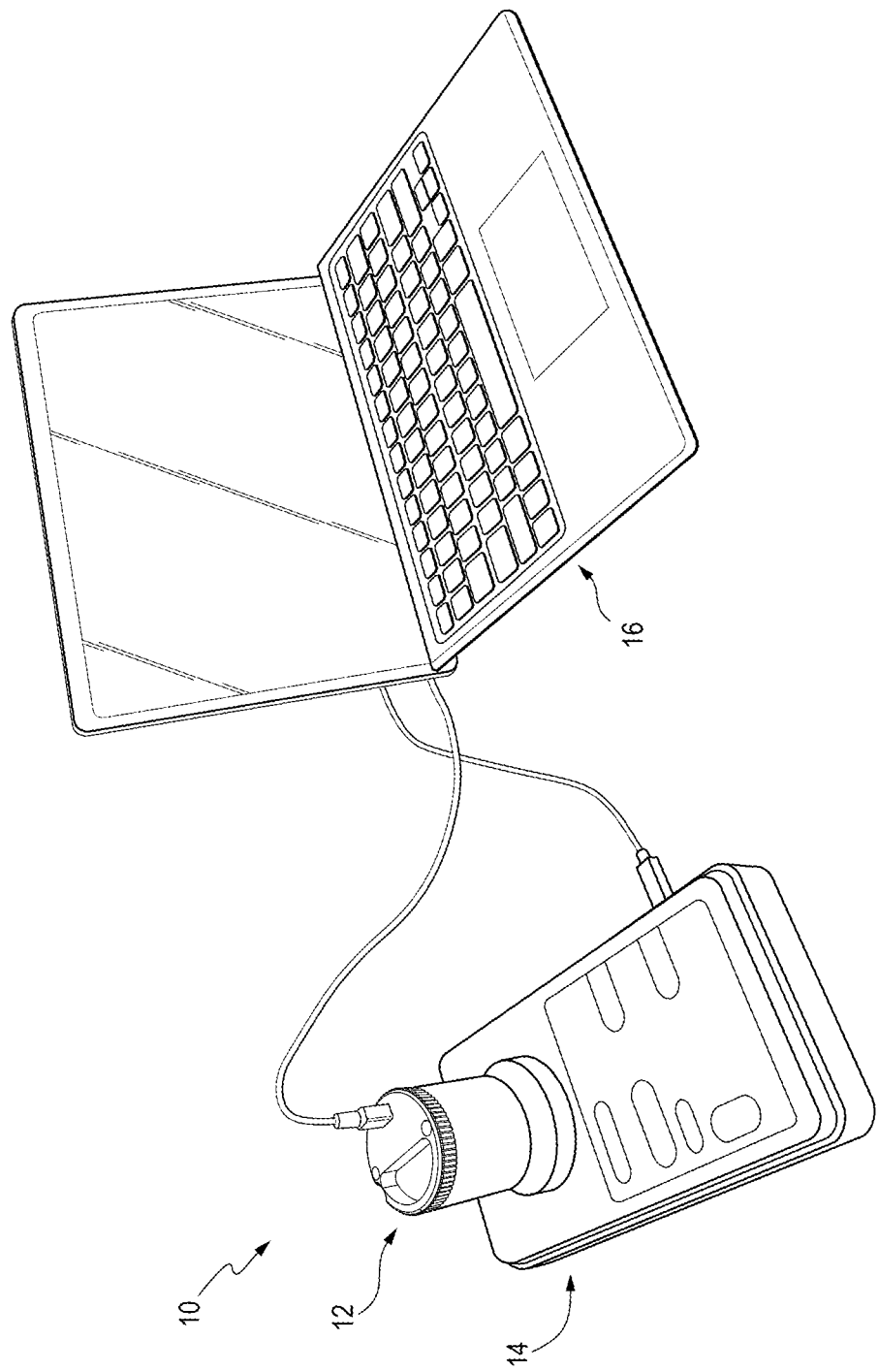
FIG. 1 is a perspective view of an electrochemistry testing system in accordance with one embodiment of the present invention.

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

The following detailed description of the invention references specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

The present invention is directed to an electrochemistry testing system and testing device that can be used in connection with the testing and analysis of specimen samples of unidentified materials. Electrochemistry is commonly used to identify unknown chemical compounds and materials by detecting electrochemical signatures that are unique to certain compounds and chemicals. These electrochemical signatures are unique wave patterns or voltammogram patterns that are specific to the specific compound or chemical and can be utilized to determine the specific identity of the compound/chemical (and/or the components thereof). Among many other uses, the testing system and testing device of the present invention can be utilized to test for quality trace detection of explosives, gun powder, accelerants, narcotics, drugs and other controlled substances, toxic industrial chemicals, contaminants, pollutants, other chemicals, and any other compounds, substances and material that can be identified through electrochemistry. Such potential uses apply themselves to, among others, law enforcement investigations, forensic science applications, airport/travel security applications, military applications, medical and healthcare applications, agronomic and soil applications, post office/customs inspections, among other applications, fields, and uses. The specimen samples may include samples from swabbed surfaces, dry material samples, liquid samples, chemical samples, urine samples, blood or other bodily fluid samples, soil samples, or any other suitable types of specimen sample, as well as combinations thereof.

Turning to FIG. 1, the electrochemistry testing system 10 of the present invention is illustrated according to one embodiment. As shown in FIG. 1, testing system 10 can include a testing receptacle device 12 and a diagnostic device 14 that can function as a testing stand or docking station for testing receptacle device 12 and/or as a diagnostic device for electrochemistry diagnostic capabilities. Testing system 10 can further include a test sensor cartridge 18 (see FIGS. 2 and 7) that can be inserted into and contained within testing receptacle device 12, and a testing swab 20 (see FIGS. 2 and 8) that can hold a specimen sample and be inserted into testing receptacle device 12 for testing as described in greater detail below. As described in greater detail herein, according to certain embodiments, testing system 12 can be used by collecting a specimen sample on a testing swab 20 and inserting the swab end 48 into testing receptacle device 12 to test the specimen sample. Alternatively, the specimen sample may be contained within an optimized liquid buffer solution (not shown) that can be poured into testing receptacle device 12 in order to test the specimen sample. Further, it will be appreciated that a liquid specimen sample may, in some cases, be poured directly into the testing receptacle device 12 without the addition of a buffer solution.

Diagnostic device test stand 14 can be configured stand for receiving, docking and/or otherwise holding testing receptacle device 12. Diagnostic device 14 can additionally or alternatively be configured as a diagnostic device, such as to include a potentiostat or galvanostat as commonly used in electrochemistry or any other suitable testing device now known or hereinafter developed and configured to operate in conjunction with testing receptacle device 12. Diagnostic device 14 and/or testing system 10 can additionally incorporate software programming that is configured to carry out the testing, analysis and scanning functionality of system 10 and display the testing results to a user through a computing device 16 (as further described below) or other user interface component as illustrated in FIG. 1. Such programming can store a library of electrochemical signatures for different types of chemicals, compounds and materials to enable system 10 to identify the composition of specimen samples tested. Diagnostic device 14 can be configured to transmit a current to a test sensor cartridge 18 within testing receptacle device 12 to test a specimen sample contained on a test swab 20 inserted into device 12 or contained in a liquid buffer solution poured into device 12 (as described in greater detail below). Diagnostic device 14 (and testing system 10 overall) can identify the composition of the tested specimen sample by determining the electrochemical signature of the sample. Cyclic voltammetry, square wave voltammetry, electrochemical impedance spectroscopy, and chronoamperometry are a few of the electrical techniques commonly used with a potentiostat or galvanostat diagnostic device, as incorporated into diagnostic device 14.

Figure 2:
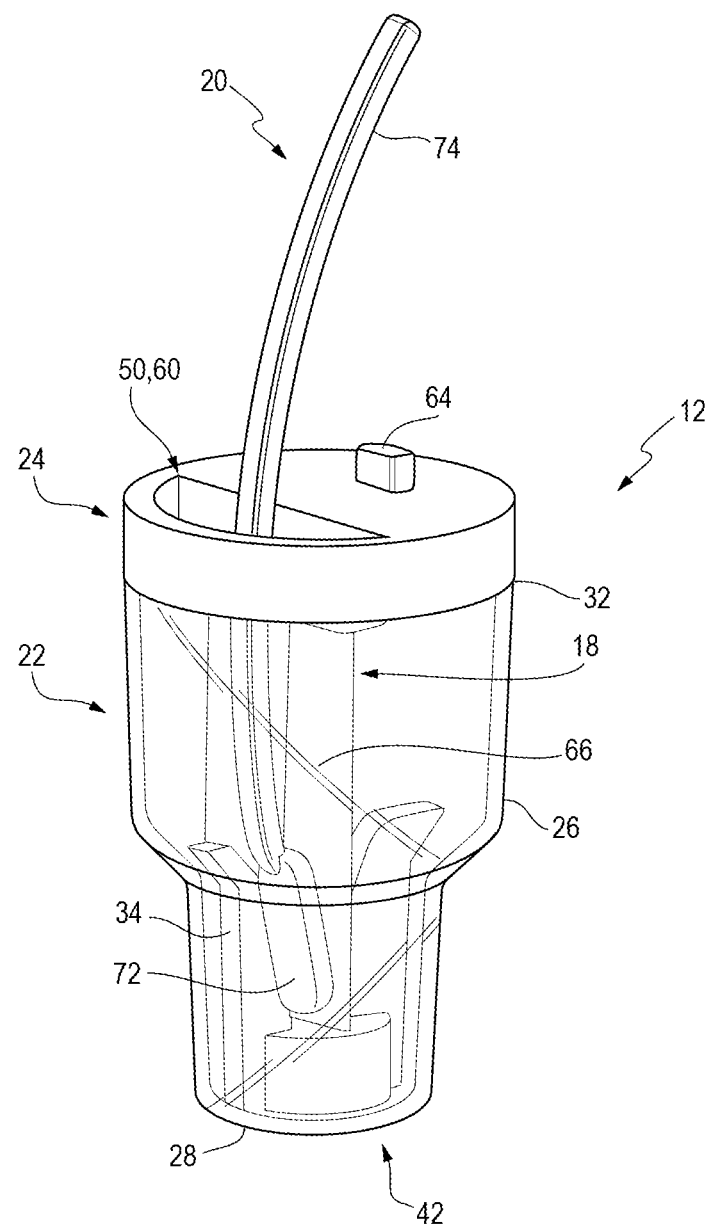
FIG. 2 is a perspective view of a testing receptacle device used in the electrochemistry testing system of FIG. 1 in accordance in accordance with one embodiment of the present invention.
Figure 3:
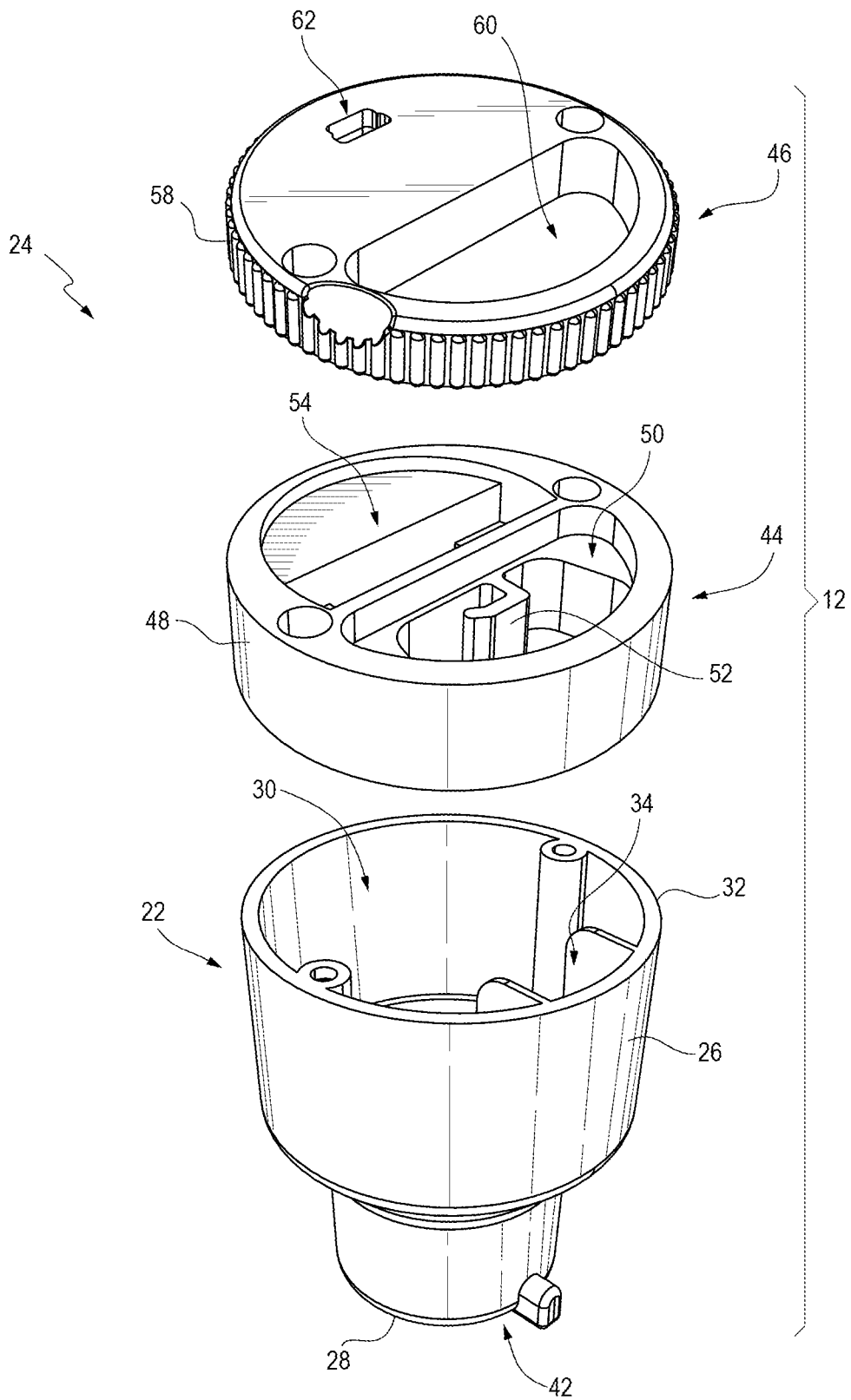
FIG. 3 is an exploded perspective view of a testing receptacle device used in the electrochemistry testing system of FIG. 1 illustrating an upper lid section, a lower lid section, and receptacle of the testing receptacle device in accordance with one embodiment of the present invention.
Figure 4:
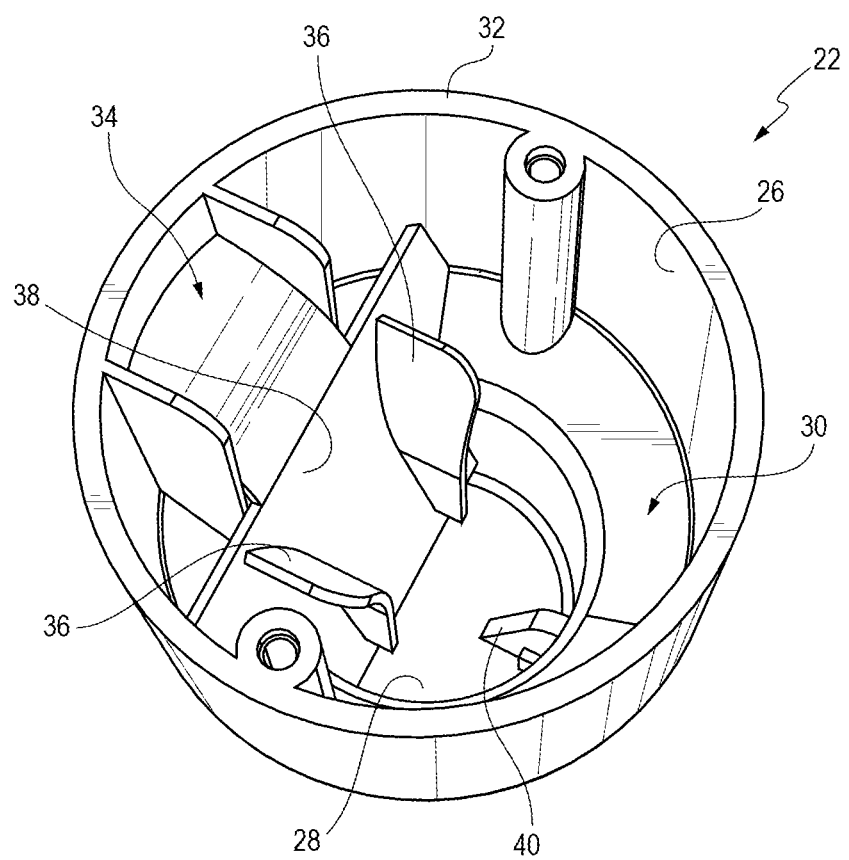
FIG. 4 is a top perspective view of the receptacle of the testing receptacle device of FIG. 3 in accordance with one embodiment of the present invention.

FIGS. 2-6 illustrate testing receptacle device 12 in accordance with one embodiment of the present invention. As best shown in FIGS. 2 and 3, testing receptacle device 12 can include a receptacle or container 22 and a lid 24 configured to fit onto the upper end of receptacle 22. As best shown in FIGS. 2-4, receptacle 22 can be configured as a vile or hollow container with a perimeter sidewall 26 and enclosed bottom wall 28 defining an interior space or volume 30. Receptacle 22 can further include an open upper end 32 configured to receive lid 24 and to allow access to the interior space 30 of receptacle 22. As shown in the figures, receptacle 22 can be configured with a cylindrical shape; however, it is recognized that receptacle 22 can be designed and constructed with any suitable shape depending on the particular embodiment of the present invention.

As best shown in FIGS. 2 and 4, receptacle 22 can include swab guide 34 formed within the interior space 30. Swab guide 34 can be configured to receive a testing swab 20 and guide the testing swab 20 toward a test sensor cartridge 18 contained within receptacle 22 as described in greater detail below. Swab guide 34 can additionally be configured to receive a liquid buffer solution inserted into test sensor cartridge 12. Swab guide 34 can extend inward from perimeter sidewall 26 be configured as an angled slot within interior space 30. According to one embodiment, swab guide 34 can include a pair of inwardly protruding fins or projections 36 extending inward along the height of perimeter sidewall 26 and toward the central region of interior space 30 as best shown in FIG. 4.

As shown in FIG. 4, swab guide 34 can further include an angled surface wall 38 defined along the interior of perimeter sidewall 26 and contained by fins 36 along each side of the angled surface wall 38 to guide a testing swab 20 toward the central region of the interior space 30 as the testing swab 20 is inserted into receptacle 22. As best shown in FIG. 4, angled surface wall 38 can originate near the interior surface of perimeter sidewall 26 toward the upper end 32 of receptacle 22. Angled surface wall 38 can then extend at a downward angle toward the lower end of receptacle 22, gradually moving closer to a central or mid-region of interior space 30. As described below, when a testing swab 20 (or a liquid buffer solution) is inserted into testing receptacle device 12, the angled surface wall 38 of swab guide 34 can force the testing swab 20 (or a liquid buffer solution) toward a central region of the interior space 30 of receptacle 22 as testing swab 20 (or a liquid buffer solution) travels further into testing receptacle device 12. In addition, fins 36 can restrict testing swab 20 (or a liquid buffer solution) from moving horizontally within interior space 30 of receptacle 22 as testing swab 20 is inserted into testing receptacle device 12.

As further shown in FIG. 4, receptacle 22 can include a test sensor cartridge retaining projection or wall 40 defined along the interior of perimeter sidewall 26 opposite swab guide 34. Retaining wall 40 can extend inward from perimeter sidewall 26 toward the central region of interior space 30 and can be configured to hold and retain test sensor cartridge 18 in a fixed position when inserted into receptacle 22.

As best shown in FIGS. 2 and 3, receptacle 22 can also include a lower end construction 42 that is configured to be received within a docking port 76 of diagnostic device 14 as described in greater detail below. Lower end construction 42 can be designed to enable testing receptacle device 12 to be retained on diagnostic device 14 when testing system 10 is in use and during storage of testing system 10. Lower end construction 22 can further include an electronic connection component (such as USB or similar connection) that can place testing receptacle device 12 in electronic communication with diagnostic 14 when lower end construction 42 is received within docking port 76 of diagnostic device 14.

Figure 5:
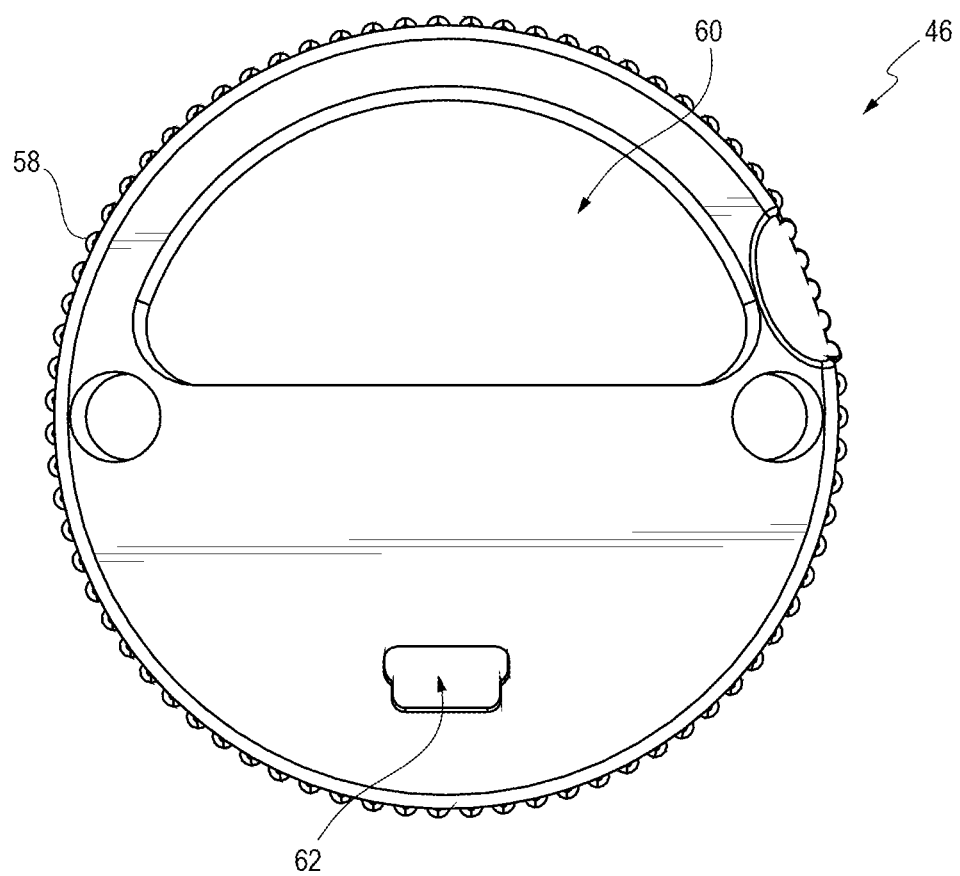
FIG. 5 is a top plan view of the upper lid section of the testing receptacle device of FIG. 3 in accordance with one embodiment of the present invention.
Figure 6:
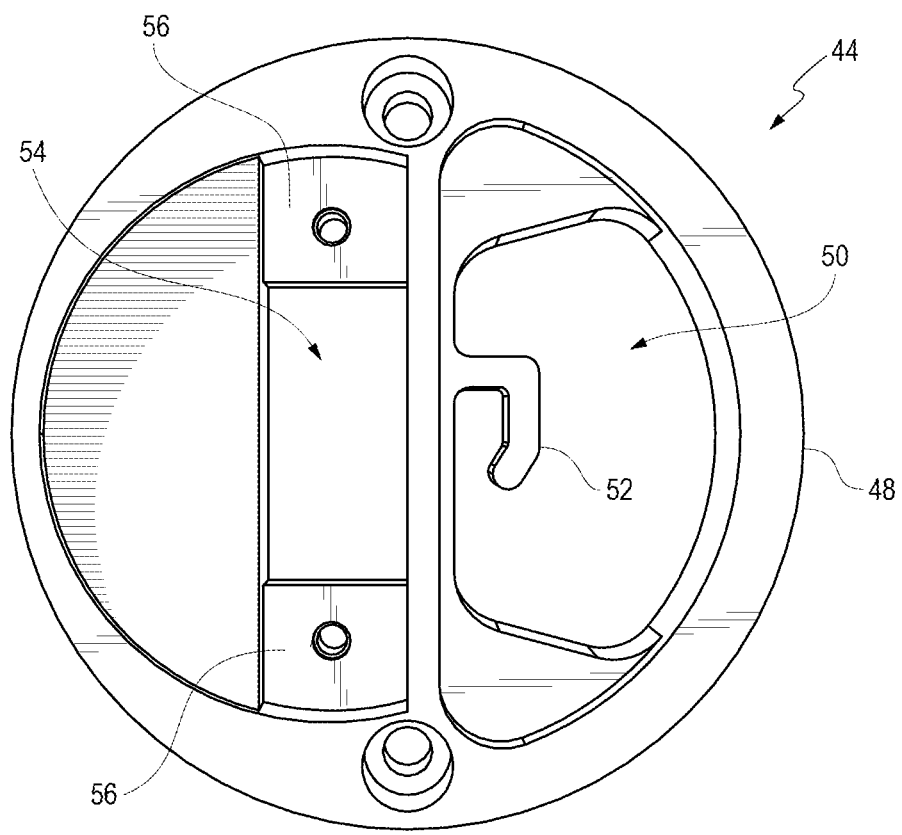
FIG. 6 is a top plan view of the lower lid section of the testing receptacle device of FIG. 3 in accordance with one embodiment of the present invention.

As best shown in FIGS. 3, 5 and 6, lid 24 of testing receptacle device 12 can include a lower lid section 44 and an upper lid section 46 collectively configured to be secured to the upper end 32 of receptacle 22. As shown in FIG. 3, lower lid section 44 and upper lid section 46 can be configured as two separable components; however, according to alternative embodiments (not shown), upper lid section 46 and lower lid section 44 can be configured as a single unitary component to form lid 24. As best shown in FIGS. 3 and 6, lower lid section 44 can include a perimeter sidewall 48 defining an upper end and lower end of lower lid section 44. Defined within the interior of lower lid section 44 can be an opening or receiving slot 50 that extends through the interior of lower lid section 44 to provide access to the interior space 30 of receptacle 22 when lid 24 is secured onto the upper end 32 of receptacle 22. Opening 50 can be configured to enable a testing swab 20 (or a liquid buffer solution) to be inserted through lid 24 and into receptacle 22 as described in greater detail below. As further shown in FIG. 6, opening 50 can include a testing swab holder 52 configured to retain a testing swab 20 in a generally fixed position once inserted through opening 50 and into receptacle 22. Testing swab holder 52 can be configured as a rectangular protrusion extending from an interior sidewall of lower lid section 44 and having a slot defined therethrough to hold and retain a testing swab 20.

As further shown in FIG. 6, lower lid section 44 can include a cartridge slot 54 opposite opening 50 that is configured to receive a test sensor cartridge 18 inserted and retained within the interior space 30 of receptacle 22 as described in greater detail below. Cartridge slot 54 can include an opening defined through the interior of lower lid section 44 and retaining walls 56 provided on each end thereof. As described in greater detail below, a test sensor cartridge 18 can be inserted partially through cartridge slot 54 and a cartridge head 68 of the test sensor cartridge 18 can be retained by the retaining walls 56 to secure the test sensor cartridge 18 to lid 24 when testing receptacle device 12 is used. The cartridge head 68 of test sensor cartridge 18 can be secured retaining walls 56 using any suitable means, including without limitation, pins, screws, bolts or other suitable means, and/or cartridge head 68 can be configured to contact and rest on retaining walls 56 without the use of any additional securement components. Cartridge slot 54 can further be configured to generally conform to the shape and dimensions of any standard test sensor cartridge design or any cartridge design desired to be used in testing system 10 so that cartridge head 68 of test sensor cartridge 18 can be adequately retained within lower lid section 44.

As best shown in FIGS. 3 and 5, upper lid section 46 can include a perimeter sidewall 58 defining an upper end and lower end of upper lid section 46. Defined within the interior of upper lid section 46 can be an opening or receiving slot 60 that extends through the interior of upper lid section 46 to provide access to the interior space 30 of receptacle 22 when lid 24 is secured onto the upper end 32 of receptacle 22. As best shown in FIG. 3, opening 60 can generally conform to the shape of opening 50 of lower lid section 44 to form a continuous opening through lid 24 and enable a testing swab 20 (or a liquid buffer solution) to be inserted through both upper lid section 46 and lower lid section 44 when lid 22 is secured onto receptacle 22.

As best shown in FIGS. 2, 3 and 5, upper lid section 46 can further include a test sensor cartridge connection slot 62 for receiving a connection port 64 of test sensor cartridge 18 once test sensor cartridge 18 is inserted into lower lid section 44. Connection port 64 can be configured to receive an input connection for powering testing receptacle device 12 (and specifically the test sensor cartridge 18 contained therein) and transmitting data to and from test sensor cartridge 18. Connection port 64 can be configured as a standard USB, micro-USB or other suitable connection type, now known or hereafter developed, depending on the particular embodiment of the present invention. Connection portion 64 can be configured to connect testing receptacle device 12 (and testing sensor cartridge 18 therein) to diagnostic device 14, computing device 16 used with testing system 10 and/or any other suitable device or component used with testing system 10. It will be appreciated that computing device 16 may take the form of a desktop computer, laptop computer, tablet, mobile device, cellular phone, handheld device, smart watch, or any other suitable computing device. It will further be appreciated that computing device 16 may be incorporated, embedded within, or otherwise form a part of the diagnostic device 14. It will further be appreciated that testing receptacle device 12, diagnostic device 14, test sensor cartridge 18, and/or computing device 16 may, in some embodiments, be in wireless communication with one another and/or other devices via Bluetooth®, a radio frequency (RF), a WiFi, 4G, LTE, 5G, infrared, Near-Field Communications (NFC) and/or other suitable wireless communication technology.

As best shown in FIG. 3, lower lid section 44 can positioned onto and secured to the upper end 32 of receptacle 22. Similarly, upper lid section 46 can be removably secured to the upper end of lower lid section 44 to form testing receptacle device 12. Upper end 32 of receptacle 22 and lower lid section 44 can include any standard or suitable interlocking means that are configured to selectively retain and secure lower lid section 44 onto upper end 32 of receptacle 22 when testing receptacle device 12 is desired to be used. Upper lid section 46 can similarly include interlocking means for selectively securing upper lid section 46 to lower lid section 44.

According to one embodiment as best illustrated in FIG. 3, upper lid section 46, lower lid section 44 and upper end 32 of receptacle 22 can each include corresponding slots or openings provided along the sides of thereof in order to receive a pin, screw or other mechanism for securing lid components 24 to receptacle 22; however, it is recognized that any suitable interlocking means may be used in various embodiments of the present invention. Upper lid section 46 can be configured to be selectively removable from lower lid section 44 in order to enable the insertion, removal and replacement of a test sensor cartridge 18 positioned within testing receptacle device 18. As further illustrated in FIGS. 2 and 3, the interlocking means used to connect upper lid section 46 to lower lid section 44 together, and subsequently lid 24 to receptacle 22, can also be configured to align upper lid section 46, lower lid section 44 and receptacle 22 together so that opening 60 of upper lid section 46, opening 50 of lower lid section 44, and swab guide 34 of receptacle 22 are all aligned together. This alignment can require a testing swab 20 (or a liquid buffer solution) inserted into testing receptacle device 12 through opening 60 to subsequently travel through opening 50 and into swab guide 34 to facilitate proper positioning of testing swab 20 (or a liquid buffer solution) when testing receptacle device 12 is used.

While not shown in the figures, according to certain embodiments of the present invention, testing receptacle device 18 may further include a cover or cap configured to be placed over opening 60 of upper lid section 46 and secured to upper lid section 46 in order to restrict dust and other particles and materials from entering testing receptacle 12 through openings 60 and 50 or upper and lower lid sections 46 and 44, respectively.

Figure 7:
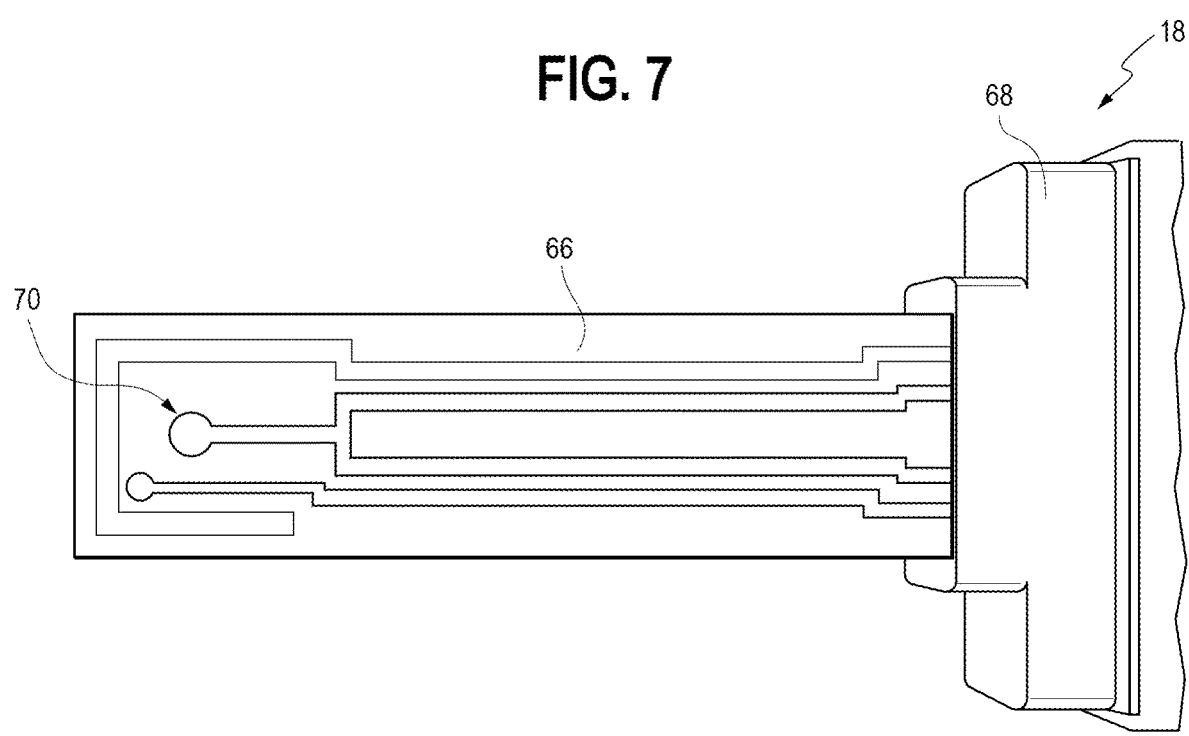
FIG. 7 is a perspective view of a testing sensor cartridge with a functionalized electrode strip used in the electrochemistry testing system of FIG. 1 in accordance with one embodiment of the present invention.

FIG. 7 illustrates a test sensor cartridge 18 configured for use in testing receptacle device 12 in accordance with one embodiment of the present invention. As shown in FIG. 7, test sensor cartridge 18 can include a functionalized electrode sensing strip 66 configured as a standard printed electrode strip (such as those commonly used for electromechanical testing and well known in the art). Test sensor cartridge 18 can further include a cartridge head 68 having integrated circuitry and a sensor strip socket for receiving the functionalized electrode sensing strip 66. Cartridge head 68 can further include connection port 64 as described above in order to connect test sensor cartridge 18 (and testing receptacle device 12) to test system 10. Test sensor cartridge 18 can be configured as a standard electrode testing cartridge suitable for use in electromechanical testing know known or hereinafter developed.

As illustrated in FIG. 7, functionalized electrode sensing strip 66 can be inserted into the socket of cartridge head 68 to place functionalized electrode testing strip 66 in communication with cartridge head 68 and further to connect to test sensor cartridge 18 to testing system 10. Test sensor cartridge 18 can operate by sending a current to testing receptacle device 22 from an external source used with testing system 10. The current can be transmitted through test sensor cartridge 18 via connection port 64 of cartridge head 68 extending through connection slot 62 of lid 24 (and subsequently functionalized electrode sensing strip 66 connected to cartridge head 68) where the electrodes are used to test a specimen sample placed in contact with the electrodes on the functionalized electrode strip 66. As further shown in FIG. 7 (as well as FIG. 2), functionalized electrode strip 66 can include a visual contact point 70 (commonly referred to as the well electrode) where a specimen sample can be positioned in order to ensure contact with the electrodes during testing as described in greater detail below.

Figure 8:
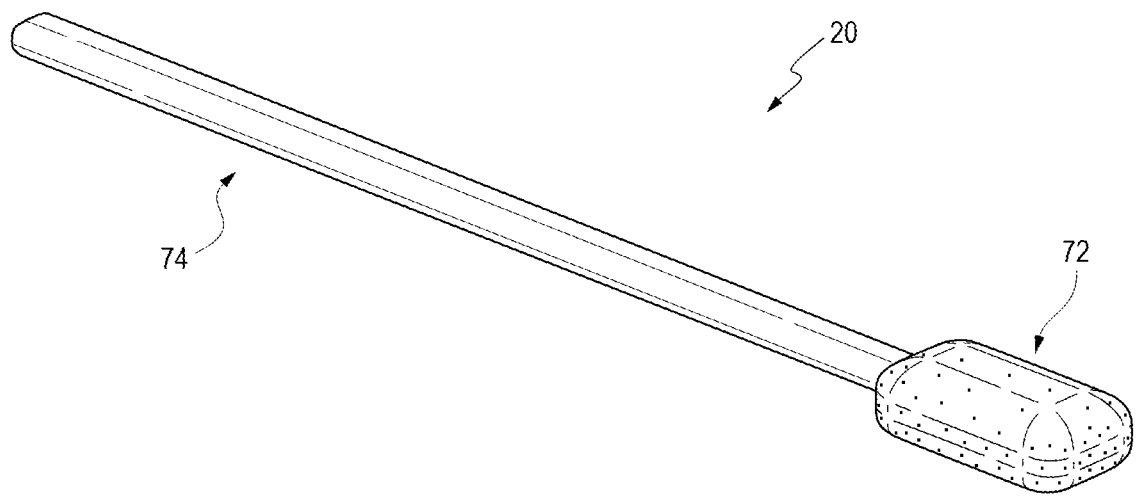
FIG. 8 is a perspective view of a testing swab used in the electrochemistry testing system of FIG. 1 in accordance with one embodiment of the present invention.

FIG. 8 illustrates a testing swab 20 configured for use with testing system 10 in accordance with one embodiment of the present invention. As shown, test swab 20 can include a swab end portion 72 and a handle or stick portion 74 extending from the swab end portion 72. Testing swab 20 can further be configured as any suitable specimen collection swab commonly used in the art. As described in greater detail below, when testing system 10 is used to test a particular specimen, a specimen sample can be collected on the swab end portion 72 and the swab end portion 72 can be inserted into testing receptacle device 12 by means of the handle portion of testing swab 20.

Figure 9:
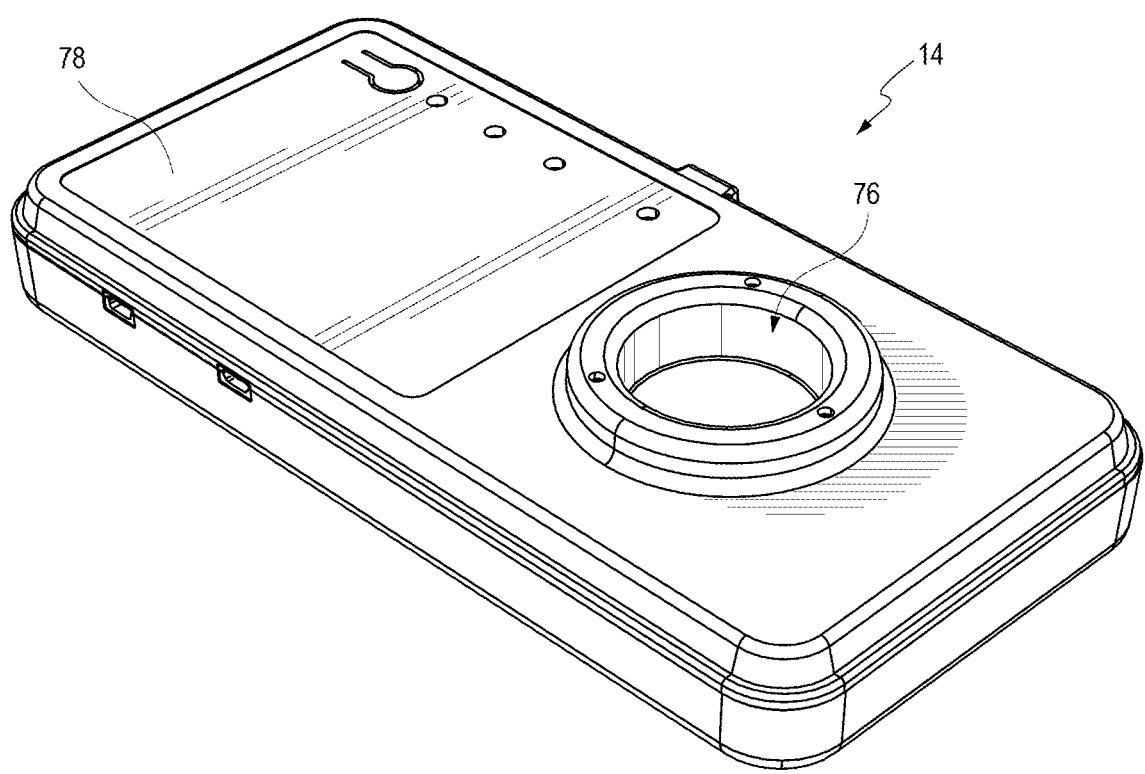
FIG. 9 is a perspective view of a diagnostic device used in the electrochemistry testing system of FIG. 1 in accordance with one embodiment of the present invention.

FIG. 9 illustrates diagnostic 14 in accordance with one embodiment of the present invention. As described above, diagnostic device 14 can be configured as diagnostic device, such as a potentiostat or galvanostat capable of carrying out cyclic voltammetry, square wave voltammetry, electrochemical impedance spectroscopy, chronoamperometry or similar electrical techniques. Diagnostic device 14 may configured with integrated circuitry and connectivity to carry such potentiostat or galvanostat functionalities. Diagnostic device 14 can be configured with one or more connection ports (see FIG. 2) to enable diagnostic device 14 to be connected to an external power source, to be electronically connected to computing device 16 (or other external computing device, display device, additional diagnostic device, or other device used with testing system 10), to be electronically connected to testing receptacle device 12, or any other suitable or desired component. Such connection ports may be configured as a standard USB, micro-USB or other suitable connection type, now known or hereafter developed. Diagnostic device 14 may include, or have embedded therein, other internal or external components of a computing device (such as input controls, soft or hard keys, displays, interactive touch screen, etc.). Diagnostic device 14 may also be configured with internal power source (such as batteries or the like) and wireless capabilities to enable the wireless transmission of data and information in addition to or in replacement of one or more connection ports. As set forth above, diagnostic device 14 may be adapted for wirelessly communicating with testing receptacle device 12, test sensor cartridge 18, computing device 16 and/or outer devices.

As best shown in FIG. 9, diagnostic device 14 can be configured with a receptacle or docking port 76 positioned within a base or platform section 78. Base section 78 may also house the internal circuitry used in the potentiostat or galvanostat diagnostic functionalities, and/or one or more storage components for holding and storing test sensor cartridges 18, testing swabs 20 or other suitable items. Docking port 78 can be configured to receive and retain lower end construction 42 of receptacle 22 to secure testing receptacle device 12 to diagnostic device 14. As best shown in FIG. 9, docking port 76 can be configured as a recessed well defined into the base section 78 to form an outer sidewall portion that generally conforms to the shape of lower end construction 42 of receptacle 22 and testing receptacle device 12. Docking port 76 and lower end construction 42 of receptacle 22 can be configured with any suitable connectivity means to place testing receptacle 12 and diagnostic device 14 in electronic communication when testing receptacle 12 is positioned onto and docked within docking port 76. Docking port 76 and lower end construction 42 of receptacle 22 can include interlocking means of any suitable type to enable testing receptacle device 12 to remain connected to diagnostic 14 via docking port 76. It is also recognized that diagnostic device 14 can also be configured to function only as a potentiostat or galvanostat diagnostic device that is connected to testing receptacle device 12 via connection port 64 within testing system 10 according certain embodiments of the present invention.

With reference to FIGS. 1 and 2, the use and application of testing system 10 (and testing receptacle device 12) will now be described in greater detail in accordance with certain embodiments of the present invention. As illustrated in FIG. 2, testing receptacle device 12 may configured with a test sensor cartridge 18 place therein. As described above, test sensor cartridge 18 may be inserted into and positioned within testing receptacle device 12 by removing upper lid section 46 from lower lid section 44 and inserting the functionalized electrode test strip 66 through cartridge slot 54 of lower lid section 44. The cartridge head 68 of testing sensor cartridge may be retained and/or secured to retaining walls 56 of cartridge slot 58 to hold cartridge head 68 in a fixed position. As further shown in FIG. 2, functionalized electrode test strip 66 can extend vertically into interior space 30 of receptacle 22 such that the lower end of electrode test strip 66 is restrained from lateral or longitudinal movement by retaining wall 40 extending inward from the interior of perimeter sidewall of receptacle 22. Functionalized electrode test strip 66 can also be orientated within inner space 30 of receptacle 22 so that contact point or well electrode 70 faces swab guide 34 within receptacle 22. Upper lid section 46 can then be re-secured to lower lid section 44.

As best shown in FIG. 1, testing receptacle device 12 can be docked into diagnostic device 14 by placing lower end construction 42 of receptacle 22 into docking port 76 of diagnostic device 14, which can place testing receptacle device 12 in electronic communication with diagnostic device 14 (testing receptacle device 12 can alternatively be connected to diagnostic device 14 through other wired or wireless connection means as described above rather than docking device 12 into docking port 76). As further shown in FIG. 1, testing receptacle device 12 and/or diagnostic device 14 can be connected to an external computing/display device 16 used with testing system 10 via the connection ports on diagnostic device 14 and connection port 64 on testing receptacle device 12 (via test sensor cartridge 18).

As best shown in FIG. 2, a testing swab 20 having a specimen sample to be tested contained on swab head portion 72 can be inserted into testing receptacle device 12. The swab end portion 74 can be inserted through opening 60 and corresponding opening 50 of the upper and lower lid sections 46 and 44, respectively, and into swab guide 34 located within receptacle 22. Swab guide 34 (via angled surface wall 38 and fins 36) requires the swab head portion 72 of testing swab 20 to move toward the lower central region of receptacle 22 and adjacent test sensing strip 66. Once testing swab 20 is fully inserted into testing receptacle device 12, swab guide 34 places the swab end portion 72 in contact with the contact point 70 of electrode test strip 66. A current can then be ran through test sensor cartridge 18 (via connection port 64 and testing receptacle device 12) to test the specimen sample on swab end 72 by means of its physical contact with contact point 70 to determine the electrochemical signature of the specimen sample. The electrochemical signature and test data can be transmitted to diagnostic device 14 (which is configured as a potentiostat or galvanostat diagnostic device) to determine the composition of the specimen sample by means of cyclic voltammetry, square wave voltammetry, electrochemical impedance spectroscopy, and chronoamperometry or other suitable electrical techniques as commonly known in the art.

In an alternative application and use of testing system 10, instead of placing the specimen sample to be tested on a testing swab 20, the specimen sample may be combined with a buffer solution and poured or drop-cast into testing receptacle device 12 (via corresponding openings 60 and 50 of lid 24) so that the solution containing the specimen sample contacts well electrode contact point 70 of functionalized electrode test strip 60 and the test may be carried out using the same steps described above.

From the foregoing, it will be seen that this invention is one well adapted to attain all the ends and objects hereinabove set forth together with other advantages which are obvious and which are inherent to the structure. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A testing system for facilitating an electrochemistry test of a specimen sample, the testing system comprising:
    a testing receptacle device comprising:
        a receptacle having a perimeter sidewall defining an interior space;
        a swab guide disposed within the interior space; the swab guide comprising an angled surface wall extending inward from an interior of the perimeter sidewall; and
        a lid configured to enclose an upper end of said receptacle, said lid having a continuous opening extending vertically through said lid, and a cartridge slot defined within the lid, the cartridge slot configured for receiving and retaining a test sensor cartridge positioned within said receptacle, the test sensor cartridge including a cartridge head and a functionalized electrode strip having an electrode well contact point at one end thereof;
    wherein the swab guide is configured to receive a specimen sample through the continuous opening of the lid and guide the specimen sample to a region of the interior space such that the specimen sample is placed in contact with the electrode well contact point of the functionalized electrode strip;
    wherein the testing system is configured to transmit an electrical current through the functionalized electrode strip for electrochemical analysis of the specimen sample.

2. The testing system of claim 1 further comprising a diagnostic device comprising a potentiostat, wherein said diagnostic device includes a docking port for receiving a lower end construction of said receptacle.

3. The testing system of claim 1, wherein said electrode well contact point of said functionalized electrode strip is positioned adjacent to a lower end of said swab guide.

4. The testing system of claim 1, wherein said swab guide is configured to receive a testing swab inserted through said continuous opening of said lid and guide said testing swab to said electrode well contact point of said functionalized electrode strip, wherein said testing swab contains said specimen sample thereon.

5. The testing system of claim 1, wherein said swab guide is configured to receive a liquid buffer solution inserted through said continuous opening of said lid and guide said liquid buffer solution to said electrode well contact point of said functionalized electrode strip, wherein said liquid buffer solution contains said specimen sample therein.

6. The testing system of claim 1, wherein the angled surface wall extends inward at an angle toward said electrode well contact point of said functionalized electrode strip.

7. The testing system of claim 6, wherein said swab guide further comprises fins provided on each side of said angled surface wall.

8. The testing system of claim 1, wherein said swab guide is aligned with said continuous opening of said lid.

9. The testing system of claim of claim 1, wherein said lid comprises an upper lid section and a lower lid section, wherein said upper lid section is removable from said lower lid section, and wherein said cartridge slot is defined within said lower lid section.

10. The testing system of claim 9, wherein said cartridge slot includes retaining walls for receiving and retaining said cartridge head of said test sensor cartridge.

11. The testing system of claim 10, wherein said upper lid section includes a connection port slot configured for receiving a connection port located on said cartridge head of said test sensor cartridge.

12. The testing system of claim 11, wherein said connection port of said test sensor cartridge is configured for connecting said testing receptacle device to a display device.

13. The testing system of claim 2, wherein said diagnostic device is configured for carrying out cyclic voltammertry, square wave voltammertry, electrochemical impedence spectrospcopy, chronoampemetry or similar electrical techniques.

14. The testing system of claim 2, wherein said docking port is configured for placing said testing receptacle device in electronic communication with said diagnostic device.

15. The testing system of claim 1, wherein said receptacle includes a retaining wall extending inward from an interior of said perimeter wall of said receptacle, wherein said retaining wall is configured for retaining said functionalized electrode strip in a fixed position.

16. A method of using the testing system of claim 1, the method comprising the steps of:
    obtaining a specimen sample on a testing swab;
    inserting a test sensor cartridge into the cartridge slot of the lid to position the functionalized electrode strip of the test sensor cartridge within the interior space of the receptacle;
    inserting the testing swab through the continuous opening of the lid;
    guiding, with the swab guide, the testing swab to a region of the interior space of the receptacle such that the testing swab is placed in contact with the electrode well contact point of the functionalized electrode strip; and
    using an electrochemical diagnostic technique on the functionalized electrode strip for electrochemical analysis of said specimen sample.

* * * * *